United States Patent [19]

Hösselbarth

[11] Patent Number: 5,685,247

[45] Date of Patent: Nov. 11, 1997

[54] MATERIAL FOR USE IN INCONTINENCE PRODUCTS

[75] Inventor: Frank Hösselbarth, Offenau, Germany

[73] Assignee: British United Shoe Machinery Limited, Leicester, England

[21] Appl. No.: 602,861

[22] PCT Filed: Aug. 16, 1994

[86] PCT No.: PCT/GB94/01794

§ 371 Date: Feb. 28, 1996

§ 102(e) Date: Feb. 28, 1996

[87] PCT Pub. No.: WO95/06560

PCT Pub. Date: Mar. 9, 1995

[30] Foreign Application Priority Data

Sep. 3, 1993 [GB] United Kingdom ............... 9318317

[51] Int. Cl.$^6$ .................. A61F 13/46; B32B 5/14; B32B 5/26; B32B 7/08
[52] U.S. Cl. .................. 112/440; 112/441; 428/91; 428/337; 428/340; 442/318; 442/319; 442/324; 442/326; 604/383
[58] Field of Search .................. 112/440, 441; 428/91, 337, 340; 442/318, 324, 326; 604/383

[56] References Cited

FOREIGN PATENT DOCUMENTS 388062  9/1990  European Pat. Off. .

Primary Examiner—James C. Cannon

[57] ABSTRACT

A multi-layer material for use in incontinence products comprises a base layer comprising a needled felt containing not less than 50% by weight polyester fiber, wherein the surface regions of the felt are denser than the central region thereof, which remains substantially unneedled. In addition, a second, multi-ply, layer is provided by a unitary fabric comprising two outer plies of knitted polyester fiber fabric with a ply of monofilament polyester accommodated therebetween. In order to prevent strike-through, furthermore, a barrier layer, e.g. of a polyurethane coated fabric, is also provided, as is also a fourth, skin-contact, layer with a nap finish to provide a comfortable "feel" to the product. Incontinence products made from this material exhibit good absorbency, little or no strike-through and a dry skin effect.

14 Claims, No Drawings

MATERIAL FOR USE IN INCONTINENCE PRODUCTS

TECHNICAL FIELD

This invention is concerned with a material for use in incontinence products, more particularly re-usable incontinence products.

BACKGROUND ART

There is described in EP-A-0 388 062 a material referred to as a "graduated density felt", which material is suitable for use in an incontinence product and comprises a needled felt containing not less than 50% by weight polyester fibre, wherein surface regions of the felt are denser than a central region thereof, which remains substantially unneedled; that is to say, in the denser surface regions the fibres are re-oriented from their original orientation by needling while the fibres in the less dense central region remain substantially in their original orientation. When in use as an incontinence product the less dense central region provides for fluid to be contained and/or absorbed therein, thereby enhancing the absorbency of the material.

Although in the aforementioned EP-A there is a proposal that 100% hydrophobic fibres be used in producing the material, in the various Examples in that specification the materials are composed of 80% by weight viscose and 20% polyester fibres. Viscose is of course hydrophilic and consequently tends to itself absorb fluid, whereas the polyester is essentially hydrophobic and does not absorb fluid. In the case of the 100% hydrophobic fibre base layer, therefore, the pool of fluid is contained within the structure of the material rather than absorbed into the individual fibres thereof. This tends to enhance the possibility of reusing the incontinence product, since now it is merely a case of washing out the fluid from the pool, rather than merely by dilution cleaning the individual absorbent fibres. Ideally, therefore, in order to produce a reusable incontinence product, the fibres used should be wholly or at least primarily hydrophobic.

It will, however, be appreciated that incontinence products have also other requirements relating e.g. to comfort for the wearer, and in particular it is desirable that the fluid be removed from contact with the skin of the wearer and be prevented from returning to the surface and wetting it, e.g. when the product is subjected to pressure, in order to avoid the wearer suffering from rashes and other skin ailments due to contact with the fluid over perhaps extended periods. The reduction of "wet-back" also reduces odours and staining and, perhaps more importantly, gives the patient more confidence when using the product.

In general, incontinence products which are commercially available have been of the disposable type, and thus not re-usable, and a common approach to the prevention of wet-back and to achieving a "dry skin effect" has been to utilise so-called "superabsorbent" polymers which tend to bind the fluid to form a gel. Such a gelling process is of course substantially irreversible and in any event washing would remove not only the gelled fluid but also the superabsorbent polymers themselves, so that with such a system a reusable incontinence product is unlikely to be achieved.

Other approaches to achieving a "dry skin effect" have also been tried, usually involving the provision of a base layer of absorbent material and an additional layer which serves to enhance comfort by speeding up the spreading of the fluid throughout the base layer. In one such case, a towelling textile has been used as the additional layer which, by reason of its absorbency, tends to effect the spreading action satisfactorily, but at the same time itself tends to retain some of the liquid, especially when the product is placed under pressure, so that in this way a dry skin effect is nevertheless not achieved using such a material.

An example of such a prior incontinence product is disclosed in U.S. Pat. No 4,516,975 (Mitchell). The diaper illustrated is a multi-layer combination of an outer moisture barrier cover and an inner facing layer for contact with a wearer. These outer and inner layers sandwich a moisture retentive felt and a middle layer to provide shape to the diaper. The moisture retentive felt is of uniform composition and depends upon rayon fibre content for absorption. Thus, once this rayon fibre content of the felt has become saturated there is a danger of wet strike-back to a wearer of the diaper.

OBJECT OF THE INVENTION

It is one of the various objects of the present invention to provide an improved material for use in incontinence products, which material provides a comfortable dry skin effect to the wearer and which is reusable by washing.

DISCLOSURE OF THE INVENTION

The invention thus provides, in one of its several aspects, a material for use in multi-layered incontinence products including a non-woven absorbent layer characterised in that the non-woven absorbent layer includes a first, base, layer comprising a needled felt containing not less than 50% by weight polyester fibre, wherein surface regions of the felt are denser than a central region thereof, which remains substantially unneedled, and the material includes a second, multi-ply, layer comprising two outer plies of polyester fabric between which is accommodated a ply of monofilament polyester, wherein the layers are joined together and the second layer serves to spread fluid applied to the product and thus enhance absorption thereof into the first layer and also to provide a barrier for the prevention of wet-back.

For the multi-ply layer constituting the second layer of the material in accordance with the invention may be used a commercially available material sold as an anti-shock material e.g. for use in shoe insoles; and available from Rökona Textilwerk GmbH, of Schaffhausenstrasse 101, 72072 Tübingen, Germany. This material, referred to as a "spacer performance material" (in German "Abstandsgewirke") is a unitary material knitted from polyester in a single piece on a two-bed knitting machine. It is available in various thicknesses and the choice of a particular thickness to be used in accordance with the present invention is dependent upon the particular product. Although this material is thus known, its use as a barrier layer for the prevention of wet-back has not previously been practised or indeed appreciated, and indeed its effectiveness as such a barrier material is both unexpected and surprising.

The German Institute for Incontinence Products (IPI) has defined a standard for wet-back performance; this standard is <2 g/10 cm$^2$ at a pressure as typically applied locally in use, viz. 4 kg/m$^2$. The disposable incontinence products referred to above are capable of meeting this standard but up to the present time no commercially available reusable product has been able to do so. By the use of a second layer as described above, the standard can now be met. Moreover the cushioning effect afforded by the second layer enhances the level of comfort to the wearer/user.

In the material in accordance with the present invention, furthermore, preferably a third layer is joined to the base layer in surface contact with the surface thereof remote from the second layer, such joining being effected about the periphery thereof, said third layer comprising a barrier layer for the prevention of the passage of fluid from the first layer through said surface. Any suitable material which is waterproof and can withstand repeated washing would be satisfactory in this case, but preferably such barrier layer is of a knitted or woven fabric coated with polyurethane, polyethylene or polyvinyl chloride, e.g. a polyurethane coated textile fabric made from 100% polyester fibres.

Also in the material in accordance with the present invention a fourth layer may be laminated to the surface of the second layer remote from the first, the fourth layer comprising a fabric having a nap on its exposed surface. This fabric will of course be in skin contact with the wearer and should therefore exhibit, in addition to a dry skin effect, a comfortable "feel". In one embodiment this fabric is a raised knitted fabric made from polyester fibres, which are of course inherently hydrophobic and thus do not detract from the dry skin effect achieved using the second, multi-ply, layer.

As already mentioned, the base layer comprises at least 50% by weight polyester fibres. It would thus be within the scope of the invention to use a base layer comprising 100% by weight polyester fibre, but in preferred examples, the base layer comprises 55 to 85% by weight polyester fibre and 15 to 45% by weight viscose. Preferably the base layer is manufactured by a method generally as set out in the aforementioned EP-A, the weight of the base layer being preferably in the region of 0.44 kg/m² and its thickness in the order of 3.0 to 6.0 mm.

The invention further provides, in another of its several aspects, an incontinence product of a multi-layered construction comprising a first, base, layer comprising a needled felt, a second layer serving to spread fluid applied to the product and thus enhance absorption thereof into the first layer and also to provide a barrier for the prevention of wet-back, a third layer joined to the base layer in surface contact with the surface thereof remote from the second layer, said third layer comprising a barrier layer for the prevention of the passage of fluid from the first layer through said surface, and a fourth layer joined to the surface of the second layer remote from the first layer, the fourth layer comprising a fabric having a nap on its exposed surface, wherein the base layer, the second layer and the barrier layer are joined together by stitching, said incontinence products being characterised in that said first layer contains not less than 50% by weight polyester fibre and wherein surface regions of the felt are denser than a central region thereof, said central region being substantially unneedled, said second layer comprising two outer plies of polyester fabric which is accommodated a ply of monofilament polyester.

For the avoidance of doubt, the term "incontinence product" where used herein is intended to include bed pads, chair pads, incontinence pads, insert pads and diapers, and indeed animal pads.

MODES FOR CARRYING OUT THE INVENTION

The invention will now be further described with reference to the following examples.

EXAMPLE I

A batt was first made up of one or more layers of a fibre blend of 60% by weight 5.0 DeciTex 40 mm staple polyester fibres and 40% by weight 1.7 DeciTex 51 mm staple viscose fibres. The batt was then needled in a four-stage operation comprising a first, pre-needling, stage, a next-following first needling stage in which needling was carried out using a down-stroke only, a second needling stage in which needling took place using an upstroke only, and a final stage in which again only a down-stroke was used. The final product weight was 0.44 kg/m² and its thickness 6.0 mm. This material constituted the base layer of the incontinence product material.

To the base layer, was then joined by stitching a second, multi-ply, layer of the type obtainable from Rökona, as referred to above. This product, which is essentially a cushioning material sold as an anti-shock material, but which has been found to be very suitable for achieving a dry skin effect, is a unitary material comprising two plies of knitted polyester fibre fabric with a third ply of monofilament polyester accommodated therebetween. In this example a 10 mm thick layer is used, providing a material suitable for use as a bed pad.

In addition, arranged in surface contact with the other surface of the first, base, layer and joined thereto, e.g. by stitching, around the periphery only thereof, is a barrier layer in the form of a polyurethane-coated woven layer of 100% polyester fibre. This material is a standard 75 g/m² polyester warp-knitted fabric coated with 250 g/m² polyurethane. Moreover, arranged adjacent the exposed surface of the second, multi-ply, layer is a woven or knitted layer of 100% polyester fibre having a nap on its exposed surface; it will of course be appreciated that this layer provides the skin-contact surface. More particularly, this layer is a standard 90 g/m² raised knitted fabric made from 100% polyester. In use, this layer is preferably joined to the second layer in the sewing operation already referred to.

The sewing operation itself is preferably a quilting operation; that is to say, the stitching is to a pattern which is decorative. Using such a pattern the "feel" of the material tends to be enhanced and in addition the pattern tends to create pathways in the material for directing the flow of the fluid contained therein.

It has been found that using a multi-layer material of this construction, the risk of strike-through is effectively eliminated and in addition by reason of the use of the second, multi-ply, layer a dry skin effect is readily achieved, while the base layer provides excellent fluid retention and the knitted polyester skin-contact layer provides a comfortable surface "feel". Tests have moreover shown that the base layer made in accordance with Example I has an absorbency of 12:1 (i.e. the fabric contains twelve times its own weight of fluid).

A material made as above has been found suitable in particular for use in the manufacture of insert pads, incotinence pads and diapers.

EXAMPLE II

In this Example the base layer is manufactured by generally the same procedure as in Example I, but in this case, while the final weight of the layer is generally the same as previously, its thickness is in this case 4.4 mm. This layer is then processed and combined as described with reference to Example I. Where the base layer is made in accordance with this Example II, its absorbency is in the order of 8:1, measured when under pressure.

In this case the material, being stronger than in the case of Example I, is suitable particularly for use in the manufacture of bed pads; typically these would be cut from the finished material to appropriate sheet sizes, e.g. 850 mm×950 mm.

In the case of either Example the barrier layer may be, instead of a polyurethane-coated fabric, a standard 75 g/m² polyester warp-knitted fabric coated with 160 g/m² polyethylene.

I claim:

1. A material for use in multi-layered incontinence products including a non-woven absorbent layer characterised in that the non-woven layer includes a first, base, layer comprising a needled felt containing not less than 50% by weight polyester fibre, wherein surface regions of the felt are denser than a central region thereof, which remains substantially unneedled, and the material includes a second, multi-ply, layer comprising two outer plies of polyester fabric between which is accommodated a ply of monofilament polyester, wherein the layers are joined together and the second layer serves to spread fluid applied to the product and thus enhance absorption thereof into the first layer and also to provide a barrier for the prevention of wet-back.

2. A material according to claim 1 wherein a further layer is joined to the surface of the second layer remote from the first layer, the further layer comprising a fabric having a nap on its exposed surface.

3. A material according to claim 2 wherein the further layer is a fabric made from polyester fibres.

4. A material according to claim 1 wherein a third layer is joined to the base layer in surface contact with the surface thereof remote from the second layer, such joining being effected about the periphery thereof, said third layer comprising a barrier layer for the prevention of the passage of fluid from the first layer through said surface.

5. A material according to claim 4 wherein the barrier layer is of a fabric material coated with one of a group comprising polyurethane, polyethylene and polyvinyl chloride.

6. A material according to claim 4 wherein the base layer, the second layer and the barrier layer are joined together by stitching.

7. A material according to claim 4 wherein a fourth layer is joined to the surface of the second layer remote from the first layer, the fourth layer comprising a fabric having a nap on its exposed surface.

8. A material according to claim 7 wherein the fourth layer is a fabric made from polyester fibres.

9. A material according to claim 1 wherein the base layer comprises 55% to 85% by weight polyester fibre and 15% to 45% by weight viscose.

10. A material according to claim 1 wherein the base layer comprises 100% by weight polyester fibre.

11. A material according to claim 9 wherein the weight of the base layer is 0.44 kg/m$^2$ and its thickness in the order of 6.0 mm.

12. A material according to claim 9 wherein the weight of the base layer is 0.44 kg/m$^2$ and its thickness in the order of 4.4 mm.

13. An incontinence product of a multi-layered construction comprising a first, base, layer comprising a needled felt, a second layer serving to spread fluid applied to the product and thus enhance absorption thereof into the first layer and also to provide a barrier for the prevention of wet-back, a third layer joined to the base layer in surface contact with the surface thereof remote from the second layer, said third layer comprising a barrier layer for the prevention of the passage of fluid from the first layer through said surface, and a fourth layer joined to the surface of the second layer remote from the first layer, the fourth layer comprising a fabric having a nap on its exposed surface, wherein the base layer, the second layer and the barrier layer are joined together by stitching, said incontinence product being characterised in that said first layer contains not less than 50% by weight polyester fibre and wherein surface regions of the felt are denser than a central region thereof, said central region being substantially unneedled, said second layer comprising two outer plies of polyester fabric which is accommodated a ply of monofilament polyester.

14. An incontinence product according to claim 13 wherein the base layer comprises 55% to 85% by weight polyester fibre and 15% to 45% by weight viscose, the barrier layer is of a fabric material coated with one of a group comprising polyurethane, polyethylene and polyvinyl chloride, and the fourth layer is a fabric made from polyester fibres.

* * * * *